US008814951B2

(12) United States Patent
Goget et al.

(10) Patent No.: US 8,814,951 B2
(45) Date of Patent: Aug. 26, 2014

(54) OXIDATION DYE COMPOSITION COMPRISING A POLYCONDENSATE OF ETHYLENE OXIDE AND OF PROPYLENE OXIDE, AND AN UNSATURATED FATTY ALCOHOL

(75) Inventors: Caroline Goget, Paris (FR); Katia Dutheil-Gouret, Les Metairies (FR); Ludivine Masselin, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/992,296

(22) PCT Filed: Dec. 6, 2011

(86) PCT No.: PCT/EP2011/071941
§ 371 (c)(1),
(2), (4) Date: Sep. 26, 2013

(87) PCT Pub. No.: WO2012/076536
PCT Pub. Date: Jun. 14, 2012

(65) Prior Publication Data
US 2014/0013521 A1 Jan. 16, 2014

Related U.S. Application Data

(60) Provisional application No. 61/424,214, filed on Dec. 17, 2010.

(30) Foreign Application Priority Data

Dec. 7, 2010 (FR) ...................... 10 60203

(51) Int. Cl.
*A61Q 5/10* (2006.01)
*A61K 8/34* (2006.01)
*A61K 8/39* (2006.01)

(52) U.S. Cl.
CPC . *A61Q 5/10* (2013.01); *A61K 8/342* (2013.01); *A61K 8/39* (2013.01)
USPC ........................ 8/405; 8/406; 8/408

(58) Field of Classification Search
CPC ................... A61K 8/39; A61Q 5/10
USPC ............................ 8/405, 406, 408
See application file for complete search history.

(56) References Cited

U.S. PATENT DOCUMENTS

| 4,003,699 A | 1/1977 | Rose et al. |
| RE30,199 E | 1/1980 | Rose et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,554,197 A | 9/1996 | Assini et al. |
| 5,663,366 A | 9/1997 | Neunhoeffer et al. |
| 5,766,576 A | 6/1998 | Lowe et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,695,887 B2 * | 2/2004 | Cottard et al. ............... 8/405 |
| 6,730,789 B1 | 5/2004 | Birault et al. |
| 7,115,147 B2 | 10/2006 | Desenne et al. |
| 7,223,294 B2 | 5/2007 | Desenne et al. |
| 2002/0010970 A1 | 1/2002 | Cottard et al. |
| 2002/0050013 A1 | 5/2002 | Vidal et al. |
| 2002/0184717 A9 | 12/2002 | Cottard et al. |
| 2003/0019051 A9 | 1/2003 | Vidal et al. |
| 2003/0192134 A1 | 10/2003 | Desenne et al. |
| 2003/0229948 A1 | 12/2003 | Desenne et al. |

FOREIGN PATENT DOCUMENTS

| DE | 2359399 | 6/1975 |
| DE | 3843892 | 6/1990 |
| DE | 4133957 | 4/1993 |
| DE | 19543988 | 5/1997 |
| EP | 0548620 | 6/1993 |
| EP | 0770375 | 5/1997 |
| EP | 1321134 | 6/2003 |
| FR | 2733749 | 11/1996 |
| FR | 2801308 | 5/2001 |
| FR | 2803196 | 6/2001 |
| FR | 2886136 | 12/2006 |
| GB | 1026978 | 4/1966 |
| GB | 1153196 | 5/1969 |
| JP | 02-19576 | 1/1990 |
| JP | 05-163124 | 5/1993 |
| WO | 9408969 | 4/1994 |
| WO | 9408970 | 4/1994 |
| WO | 9615765 | 5/1996 |

OTHER PUBLICATIONS

International Search Report for PCT/EP2011/071941.
PCT/IB/308 Form for PCT/EP2011/071941.
Edens, Michael W., et al., "Applications of Block Copolymer Surfactants," Developments in Block Copolymer Science and Technology, Wiley & Sons, Ltd., (XP001233807), Jan. 2004, pp. 326-340.

* cited by examiner

*Primary Examiner* — Eisa Elhilo
(74) *Attorney, Agent, or Firm* — The Marbury Law Group, PLLC

(57) ABSTRACT

The present invention relates to a dye composition comprising: * at least one oxidation dye precursor; * at least one polycondensate of ethylene oxide and of propylene oxide having the structure (A) below $H—(O—CH_2—CH_2)_n—(O—CH(CH_3)—CH_2)_b—(O—CH_2—CH_2)_a—OH$ (A) in which formula a and a' range from 2 to 150 and b ranges from 1 to 100; and * at least one $C_8$-$C_{30}$ fatty alcohol comprising at least one unsaturation. The invention also relates to a dyeing process using this composition (free of oxidizing agent) after mixing with a composition comprising an oxidizing agent. Another subject of the invention is a two-compartment device, the first compartment comprising the composition according to the invention, free of oxidizing agent, and the second compartment containing a composition comprising at least one oxidizing agent.

19 Claims, No Drawings

OXIDATION DYE COMPOSITION COMPRISING A POLYCONDENSATE OF ETHYLENE OXIDE AND OF PROPYLENE OXIDE, AND AN UNSATURATED FATTY ALCOHOL

This is a national stage application of PCT/EP2011/071941, filed internationally on Dec. 6, 2011, which claims priority to U.S. Provisional Application No. 61/424,214, filed on Dec. 17, 2010; as well as French Application FR 1060203, filed on Dec. 7, 2010.

The present invention relates to a composition for dyeing human keratin fibres, especially the hair. The invention also relates to a dyeing process using this composition, and to a multi-compartment device containing it.

Among the methods for dyeing human keratin fibres, such as the hair, mention may be made of oxidation dyeing or permanent dyeing. More particularly, this dyeing method uses one or more oxidation dyes and usually one or more oxidation bases optionally combined with one or more couplers.

In general, oxidation bases are chosen from ortho- or para-phenylenediamines, ortho- or para-aminophenols and heterocyclic compounds. These oxidation bases are colourless or weakly coloured compounds which, when combined with oxidizing products, can give access to coloured species.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colours to be obtained.

It is also possible to add to these compositions direct dyes, which are coloured, and colouring molecules that have affinity for fibres. The direct dyes generally used are chosen from nitrobenzene, anthraquinone, nitropyridine, azo, methine, azomethine, xanthene, acridine, azine and triarylmethane direct dyes. The presence of such compounds enables the obtained coloration to be further enriched with tints or enables the chromaticity of the obtained coloration to be increased.

Oxidation dyeing processes thus consist in using with these dye compositions a composition comprising at least one oxidizing agent, generally hydrogen peroxide, under alkaline pH conditions in the vast majority of cases. The role of this oxidizing agent is to reveal the coloration, via an oxidative condensation reaction between the oxidation dyes.

Oxidation dye must moreover satisfy a certain number of requirements. Thus, it must be free of toxicological drawbacks, it must enable shades to be obtained in the desired intensity and it must show resistance to external attacking factors such as light, bad weather, washing, permanent waving, or perspiration and rubbing.

The dyes must also be able to cover grey hair and, finally, they must be as unselective as possible, i.e. they must produce the smallest possible colour differences along the same keratin fibre, which generally comprises areas that are differently sensitized (i.e. damaged) from its end to its root.

It is common practice to use dye compositions containing particular polymers and surfactant systems directed towards the stability of the composition and to maintenance of its viscosity, in order to keep the dye composition on the hair during the time of reaction/penetration of the dyes into the keratin fibre and to limit the risks of running onto the face.

It has moreover been recommended to use surfactants, in particular nonionic surfactants, in oxidation dyeing and especially in dyeing products that are in the form of liquids containing oxidation dye precursors to be mixed with oxidizing compositions, which are liquid compositions in which the proportions of these surfactants are often large. To obtain satisfactory application conditions after mixing these liquid compositions with the oxidizing compositions, especially with a viscosity that is sufficient to prevent running, it most often proves necessary to thicken slightly the said liquid compositions. Unfortunately, the majority of thickening polymers lead to rapid demixing of the composition. Moreover, very often, the viscosity-increasing power of the polymers is very greatly reduced when they are combined with relatively large amounts of surfactants.

One of the aims of the present invention is thus to obtain a composition for dyeing the hair, which is stable over time and which remains localized on the hair during application, without running, while at the same time conserving the dyeing properties obtained on the hair, in particular conserving powerful, chromatic and uniform colorations between the end and the root of the same fibre and from one fibre to another.

This aim is achieved by the present invention, one subject of which is a dye composition comprising at least one oxidation dye precursor, at least one polycondensate of ethylene oxide and of propylene oxide having the chemical formula (A) below:

$$H-(O-CH_2-CH_2)_a-(O-CH(CH_3)-CH_2)_b-(O-CH_2-CH_2)_{a'}-OH \quad (A)$$

in which a and a' range from 2 to 150 and b ranges from 1 to 100, and at least one $C_8$-$C_{30}$ fatty alcohol comprising at least one unsaturation.

The invention also relates to a hair dyeing process that consists in applying to the fibres the composition of the invention, in the presence of an oxidizing agent.

A subject of the invention is also a two-compartment device containing, in one of the compartments, the composition of the invention as defined above (free of oxidizing agent) and, in the other compartment, a composition comprising at least one oxidizing agent.

Thus, the invention makes it possible to obtain a thickened composition that is stable over time, which remains in place after application on the hair, without the risk of running. In addition, this composition has improved dyeing properties.

According to the invention, the term "at least one" is equivalent to "one or more".

Unless otherwise indicated, the limits of a range of values are included within that range.

As indicated previously, the composition according to the invention comprises at least one polyethylene glycol/polypropylene glycol/polyethylene glycol triblock polycondensate.

Advantageously, the polycondensate of ethylene oxide and of propylene oxide of formula (A) corresponds to a polyethylene glycol/polypropylene glycol/polyethylene glycol triblock polycondensate.

Preferably, in the chemical structure (A) described above, a and a' range from 10 to 130 and b ranges from 20 to 80. In accordance with an even more particular embodiment, a and a' range from 50 to 130 and b ranges from 30 to 80, and preferably a and a' range from 80 to 130 and b ranges from 40 to 80. According to one particular embodiment, a and a' are identical.

The polycondensate of ethylene oxide and of propylene oxide that is useful in the composition of the invention preferably has a weight-average molecular weight ranging from 250 to 19 000, better still ranging from 1200 to 15 000, in particular ranging from 1500 to 10 000 and even better still ranging from 1500 to 5000.

Advantageously, the said polycondensate of ethylene oxide and of propylene oxide has a cloud point, at 10 g/l in distilled water, of greater than or equal to 20° C. and preferably of greater than or equal to 60° C. The cloud point is measured according to standard ISO 1065.

As polycondensates of ethylene oxide and of propylene oxide that may be used according to the invention, mention may be made of the polyethylene glycol/polypropylene glycol/polyethylene glycol triblock polycondensates sold under the name Synperonic, for instance Synperonic® PE/F32 (INCI name: Poloxamer 108), Synperonic® PE/F108 (INCI name: Poloxamer 338), Synperonic® PE/L44 (INCI name: Poloxamer 124), Synperonic® PE/L42 (INCI name: Poloxamer 122), Synperonic® PE/F127 (INCI name: Poloxamer 407), Synperonic® PE/F88 (INCI name: Poloxamer 238), Synperonic® PE/L64 (INCI name: Poloxamer 184), Synperonic® PE/F88 (INCI name: Poloxamer 238), Synperonic® PE/F87 (INCI name: Poloxamer 237) from the company Croda, or Lutrol® F68 (INCI name: Poloxamer 188) by the company BASF.

According to one embodiment of the invention, the amount of polycondensates of ethylene oxide and of propylene oxide preferably ranges from 0.1% to 20% by weight, even more preferentially from 0.5% to 10% by weight and better still from 1% to 5% by weight relative to the total weight of the composition.

The oxidation dyes that are useful in the composition of the invention are generally chosen from oxidation bases and couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis($\beta$-hydroxyethyl)-para-phenylenediamine, 4-N,N-bis($\beta$-hydroxyethyl)amino-2-methylaniline, 4-N,N-bis($\beta$-hydroxyethyl)amino-2-chloroaniline, 2-$\beta$-hydroxyethyl-para-phenylenediamine, 2-fluoro-para-phenylenediamine, 2-isopropyl-para-phenylenediamine, N-($\beta$-hydroxypropyl)-para-phenylenediamine, 2-hydroxymethyl-para-phenylenediamine, N,N-dimethyl-3-methyl-para-phenylenediamine, N,N-(ethyl-$\beta$-hydroxyethyl)-para-phenylenediamine, N-($\beta$,$\gamma$-dihydroxypropyl)-para-phenylenediamine, N-(4'-aminophenyl)-para-phenylenediamine, N-phenyl-para-phenylenediamine, 2-$\beta$-hydroxyethyloxy-para-phenylenediamine, 2-$\beta$-acetylaminoethyloxy-para-phenylenediamine, N-($\beta$-methoxyethyl)-para-phenylenediamine, 4-aminophenylpyrrolidine, 2-thienyl-para-phenylenediamine, 2-$\beta$-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-$\beta$-hydroxyethyl-para-phenylenediamine, 2-$\beta$-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis($\beta$-hydroxyethyl)-para-phenylenediamine, 2-chloro-para-phenylenediamine and 2-$\beta$-acetylaminoethyloxy-para-phenylenediamine, and the addition salts thereof with an acid, are particularly preferred.

Among the bis(phenyl)alkylenediamines that may be mentioned, for example, are N,N'-bis($\beta$-hydroxyethyl)-N,N'-bis(4'-aminophenyl)-1,3-diaminopropanol, N,N'-bis-($\beta$-hydroxyethyl)-N,N'-bis(4'-aminophenyl)ethylenediamine, N,N'-bis(4-aminophenyl)tetramethylenediamine, N,N'-bis($\beta$-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethyl phenol, 4-amino-2-aminomethylphenol, 4-amino-2-$\beta$-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethyl-pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-β-hydroxyethyl) amino-1-methylpyrazole, and the addition salts thereof. 4,5-Diamino-1-(β-methoxyethyl)pyrazole may also be used. A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a] pyrazol-1-one, 2-amino-3-isopropylamino-6,7-dihydro-1H, 5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H, 5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1, 2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one, 2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylamino-benzene, sesamol, 1β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxy-pyridine, 1-N-(β-hydroxyethyl)amino-3,4-methylenedioxybenzene, 2,6-bis(β-hydroxy-ethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]-benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

According to one embodiment, the composition comprises at least one oxidation base and optionally a coupler.

The oxidation base(s) each advantageously represent from 0.0001% to 10% by weight relative to the total weight of the composition, and preferably from 0.005% to 5% by weight relative to the total weight of the composition.

The content of coupler(s), if it is (they are) present, each advantageously represent from 0.0001% to 10% by weight relative to the total weight of the composition, and preferably from 0.005% to 5% by weight relative to the total weight of the composition.

The composition of the invention also comprises at least one $C_8$-$C_{30}$ fatty alcohol comprising at least one unsaturation, more particularly from 1 to 3 unsaturations (carbon-carbon). Preferably, the fatty alcohol comprises from 12 to 22 carbon atoms.

The fatty alcohols of the invention are non-oxyalkylenated and non-glycerolated.

The terms "non-oxyalkylenated" and "non-glycerolated" mean compounds that do not comprise the following units in their structure:
—CH2-CH2-O—
—CH2-CH(CH3)-O—
—CH2-CH2-CH2-O—
—CH2-CH(CH2OH)—O—

As examples of unsaturated fatty alcohols according to the invention, mention may be made especially of oleyl alcohol, linoleyl alcohol, undecylenyl alcohol, palmitoleyl alcohol, linolenyl alcohol, arachidonyl alcohol and erucyl alcohol, alone or as mixtures; and preferably oleyl alcohol.

The unsaturated fatty alcohol(s) advantageously represent from 0.1% to 15% by weight, preferably from 0.5% to 10% by weight and better still from 1% to 5% by weight relative to the total weight of the dye composition.

Preferably, the $C_8$-$C_{30}$ fatty alcohol(s) comprising at least one unsaturation/polycondensate(s) of formula (A) weight ratio ranges from 0.1 to 10, even more preferentially from 0.2 to 5 and better still from 0.5 to 2.

The composition according to the invention may optionally comprise synthetic or natural dyes, chosen from ionic or nonionic species, preferably cationic or nonionic species.

Examples of suitable direct dyes that may be mentioned include azo dyes; methine dyes; carbonyl dyes; azine dyes; nitro (hetero)aryl dyes; tri(hetero)arylmethane dyes; porphyrin dyes; phthalocyanine dyes, and natural direct dyes, alone or as mixtures.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts, may also be used.

When they are present, the direct dye(s) more particularly represent from 0.0001% to 10% by weight and preferably from 0.005% to 5% by weight of the total weight of the composition.

The medium that is suitable for dyeing, also known as the dye support, generally comprises water or a mixture of water and of one or more organic solvents, for example $C_1$-$C_4$ lower alkanols such as ethanol and isopropanol, polyols, for instance propylene glycol, dipropylene glycol or glycerol, and polyols, for instance dipropylene glycol monomethyl ether.

According to one particular embodiment, the composition of the invention comprises a $C_1$-$C_4$ aliphatic alcohol, especially ethanol or isopropanol.

These solvents are generally present in proportions that may be between 1% and 40% by weight and even more preferentially between 3% and 30% by weight relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral thickeners such as silicates or organic thickeners, and in particular anionic, cationic, nonionic and am photeric polymeric associative thickeners, antioxidants, penetrating agents, sequestering agents, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 5 and 14 approximately and preferably greater than 5.

According to one particular embodiment, the pH is between 6 and 11.

It may be adjusted to the desired value by means of acidifying or basifying agents usually used in the dyeing of keratin fibers, or alternatively using standard buffer systems.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Mention may be made, among the basifying agents, by way of example, of aqueous ammonia, alkaline carbonates, alkanolamines, such as mono-, di- and triethanolamines, and their derivatives, sodium hydroxide, potassium hydroxide and the compounds with the following formula:

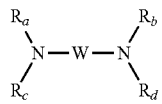

in which W is a propylene residue optionally substituted with a hydroxyl group or a $C_1$-$C_4$ alkyl radical; Ra, Rb, Rc and Rd, which may be identical or different, represent a hydrogen atom or a $C_1$-$C_4$ alkyl or $C_1$-$C_4$ hydroxyalkyl radical.

Advantageously, the composition according to the invention has a content of basifying agent(s) ranging from 0.01% to 30% by weight and preferably from 0.1% to 20% by weight relative to the weight of the composition.

According to one embodiment, the composition comprises at least one alkaline agent.

The composition according to the invention may comprise one or more oxidizing agents. Conventionally, the oxidizing agent is added to the composition at the time of use.

More particularly, the oxidizing agent(s) are chosen from hydrogen peroxide, urea peroxide, alkali metal bromates or ferricyanides, peroxygenated salts, for instance alkali metal or alkaline-earth persulfates, perborates and percarbonates, and also peracids and precursors thereof.

Advantageously, the oxidizing agent is hydrogen peroxide.

The content of oxidizing agent(s) more particularly represents from 0.1% to 20% by weight and preferably from 0.5% to 10% by weight relative to the weight of the composition.

Preferably, the oxidizing agent is hydrogen peroxide in aqueous solution, the concentration of which ranges, more particularly, from 0.1% to 50% by weight, more particularly between 0.5% and 20% by weight and even more preferentially between 1% and 15% by weight relative to the weight of the oxidizing composition.

Preferably, the composition of the invention before mixing with the oxidizing agent is in liquid form at a temperature of 25° C. and at atmospheric pressure (760 mmHg), i.e. it is capable of flowing under the action of its own weight.

Preferably, the viscosity at a temperature of 25° C. and at a shear rate of 1 s$^{-1}$ of the composition of the invention before mixing with the oxidizing agent is between $10^{-2}$ Pa·s and 5 Pa·s and preferably between $10^{-1}$ Pa·s and 2 Pa·s. It may be measured using a Thermo Haake RS600 rheometer with cone-plate geometry or an equivalent machine.

Preferably, the composition of the invention before mixing with the oxidizing agent contains a total amount of ionic or nonionic surfactants of greater than 8% and even more preferentially greater than 10%.

The dyeing process according to the invention thus consists in mixing a composition (free of oxidizing agent) comprising at least one dye precursor, at least one polycondensate of polyethylene and of polypropylene as defined previously, and at least one C8-C30 fatty alcohol comprising at least one unsaturation, with a composition comprising an oxidizing agent, and in applying this composition to wet or dry human keratin fibres.

The composition is then left in place for a time usually ranging from one minute to one hour and preferably from 5 minutes to 30 minutes.

The temperature during the process is conventionally between room temperature (between 15 and 25° C.) and 80° C. and preferably between room temperature and 60° C.

After the treatment, the human keratin fibres are optionally rinsed with water, optionally washed with a shampoo and then rinsed with water, before being dried or left to dry.

EXAMPLES

The following compositions were prepared:

| Composition A | % by weight (AM) |
|---|---|
| 1,4-Diaminobenzene | 0.36 |
| 2-Methyl-1,3-dihydroxybenzene | 0.15 |
| 1,3-Dihydroxybenzene | 0.77 |
| 6-Hydroxyindole | 0.07 |
| 1-Hydroxy-3-aminobenzene | 0.41 |
| Rapeseed fatty acid amide 4 OE (PEG-4 rapeseed amide) | 8.12 |
| Decyl alcohol 3 OE (Deceth-3) | 6.93 |
| Monoglycerolated lauryl alcohol (glyceryl lauryl ether) | 7 |
| Oleyl alcohol | 1.1 |
| Laureth-5 carboxylic acid | 4.5 |
| Ethanolamine | 3.66 |
| EDTA | 0.2 |
| Ethanol | 8.2 |
| Propylene glycol | 6.2 |
| Hexylene glycol | 3 |
| Dipropylene glycol | 3 |
| POE/POP/POE (Poloxamer 338 sold by BASF; a = a' = 128 b = 54) | 2 |
| Polyquaternium-6 | 1.36 |
| Ammonium thiolactate | 0.464 |
| Erythorbic acid | 0.12 |
| Ammonium hydroxide | 2.88 |
| Water | qs 100 |

(AM): Active Material

| Composition B | % by weight (AM) |
|---|---|
| 1,4-Diaminobenzene | 0.36 |
| 2-Methyl-1,3-dihydroxybenzene | 0.15 |
| 1,3-Dihydroxybenzene | 0.77 |
| 6-Hydroxyindole | 0.07 |
| 1-Hydroxy-3-aminobenzene | 0.41 |
| Rapeseed fatty acid amide 4 OE (PEG-4 rapeseed amide) | 9.23 |
| Decyl alcohol 3 OE (Deceth-3) | 6.93 |
| Monoglycerolated lauryl alcohol (glyceryl lauryl ether) | 7 |
| Oleyl alcohol | 1.1 |
| Laureth-5 carboxylic acid | 4.5 |
| Ethanolamine | 2.91 |
| EDTA | 0.2 |
| Ethanol | 8.2 |
| Propylene glycol | 6.2 |
| Hexylene glycol | 3 |
| Dipropylene glycol | 3 |
| POE/POP/POE (Poloxamer 338 sold by BASF; a = a' = 128 b = 54) | 2 |
| Polyquaternium-6 | 1.36 |
| Thiolactic acid | 0.251 |
| Erythorbic acid | 0.12 |
| Water | qs 100 |

(AM): Active Material

| Composition C | % by weight (AM) |
|---|---|
| 1,4-Diaminobenzene | 0.36 |
| 2-Methyl-1,3-dihydroxybenzene | 0.15 |
| 1,3-Dihydroxybenzene | 0.77 |
| 6-Hydroxyindole | 0.07 |
| 1-Hydroxy-3-aminobenzene | 0.41 |
| Rapeseed fatty acid amide 4 OE (PEG-4 rapeseed amide) | 8.12 |
| Decyl alcohol 3 OE (Deceth-3) | 6.93 |
| Monoglycerolated lauryl alcohol (glyceryl lauryl ether) | 7 |
| Oleyl alcohol | 1.1 |
| Laureth-5 carboxylic acid | 4.5 |
| Ethanolamine | 5.66 |
| EDTA | 0.2 |
| Ethanol | 8.2 |
| Propylene glycol | 6.2 |
| Hexylene glycol | 6 |
| POE/POP/POE (Poloxamer 338 sold by BASF; a = a' = 128 b = 54) | 2 |
| Polyquaternium-6 | 1.36 |
| Thiolactic acid | 0.251 |
| Erythorbic acid | 0.12 |
| Water | qs 100 |

(AM): Active Material

Compositions A, B and C are stable over time.

Each of them is mixed with 1.5 times its own weight of an oxidizing composition comprising 7.5% hydrogen peroxide at pH 2.

The mixtures obtained apply easily to dark chestnut-brown hair, without running.

After a leave-on time of 30 minutes at 25° C. followed by rinsing, the hair is washed and dried.

The hair is then uniformly dyed in a strong golden light chestnut-brown colour with the two mixtures obtained from compositions A, B and C.

The invention claimed is:

1. A dye composition comprising
   at least one oxidation dye precursor;
   at least one polycondensate of ethylene oxide and of propylene oxide of formula (A):

$$H-(O-CH_2-CH_2)_a-(O-CH(CH_3)-CH_2)_b-(O-CH_2-CH_2)_{a'}-OH \quad (A)$$

wherein a and a' range from 2 to 150 and b ranges from 1 to 100; and
   at least one $C_8$-$C_{30}$ fatty alcohol comprising at least one unsaturation;
   wherein the weight ratio of the at least one $C_8$-$C_{30}$ fatty alcohol comprising at least one unsaturation to the at least one polycondensate of ethylene oxide and of propylene oxide ranges from about 0.1 to about 10.

2. The dye composition according to claim 1, wherein the at least one oxidation dye precursor is at least one oxidation base chosen from para-phenylenediamines, bis(phenyl)alkylenediamines, para-aminophenols, ortho-aminophenols, heterocyclic bases, and the addition salts thereof, and optionally at least one coupler chosen from meta-phenylenediamines, meta-aminophenols, meta-diphenols, naphthalene-based couplers, heterocyclic couplers, and the addition salts thereof.

3. The dye composition according to claim 1, wherein for the at least one polycondensate of ethylene oxide and of propylene oxide, a and a' range from 10 to 130 and b ranges from 20 to 80.

4. The dye composition according to claim 1, wherein for the at least one polycondensate of ethylene oxide and of propylene oxide, a and a' range from 80 to 130 and b ranges from 40 to 80.

5. The dye composition according to claim 1, wherein for the at least one polycondensate of ethylene oxide and of propylene oxide, a and a' and are identical.

6. The dye composition according to claim 1, wherein the amount of the at least one polycondensate of ethylene oxide and of propylene oxide ranges from about 0.1% to about 20% by weight, relative to the total weight of the composition.

7. The dye composition according to claim 1, wherein the amount of the at least one polycondensate of ethylene oxide and of propylene oxide ranges from about 1% to about 5% by weight, relative to the total weight of the composition.

8. The composition according to claim 1, wherein the at least one $C_8$-$C_{30}$ fatty alcohol comprising at least one unsaturation is chosen from $C_{12}$-$C_{22}$ alcohols comprising from 1 to 3 unsaturations.

9. The dye composition according to claim 1, wherein the at least one $C_8$-$C_{30}$ fatty alcohol comprising at least one unsaturation is chosen from oleyl alcohol, linoleyl alcohol, undecylenyl alcohol, palmitoleyl alcohol, linolenyl alcohol, arachidonly alcohol and erucyl alcohol.

10. The dye composition according to claim 1, wherein the at least one $C_8$-$C_{30}$ fatty alcohol comprising at least one unsaturation is oleyl alcohol.

11. The dye composition according to claim 1, wherein the at least one $C_8$-$C_{30}$ fatty alcohol comprising at least one unsaturation is present in an amount ranging from about 0.1% to about 15% by weight, relative to the total weight of the composition.

12. The dye composition according to claim 1, wherein the at least one $C_8$-$C_{30}$ fatty alcohol comprising at least one unsaturation is present in an amount ranging from about 1% to about 5% by weight, relative to the total weight of the composition.

13. The dye composition according to claim 1, wherein the weight ratio of the at least one $C_8$-$C_{30}$ fatty alcohol comprising at least one unsaturation to the at least one polycondensate of ethylene oxide and of propylene oxide ranges from about 0.5 to about 2.

14. The dye composition according to claim 1, wherein the dye composition is liquid at about 25° C. and at atmospheric pressure.

15. The dye composition according to claim 1, further comprising a total amount of ionic or nonionic surfactants of greater than about 8%.

16. The dye composition according to claim 1, further comprising a total amount of ionic or nonionic surfactants of greater than about 10%.

17. The dye composition according to claim 1, further comprising at least one oxidizing agent.

18. A process for dyeing hair, comprising:
(1) mixing:
   (a) at least one oxidizing agent and
   (b) a composition comprising:
      (i) at least one oxidation dye precursor and
      (ii) at least one polycondensate of ethylene oxide and of propylene oxide of formula (A):

wherein a and a' range from 2 to 150 and b ranges from 1 to 100, and
      (iii) at least one $C_8$-$C_{30}$ fatty alcohol comprising at least one unsaturation;
      wherein the weight ratio of the at least one $C_8$-$C_{30}$ fatty alcohol comprising at least one unsaturation to the at least one polycondensate of ethylene oxide and of propylene oxide ranges from about 0.1 to about 10; and
(2) applying the resultant mixture to hair.

19. A two-compartment device comprising:
in a first compartment, a first composition comprising at least one oxidation dye precursor, at least one polycondensate of ethylene oxide and of propylene oxide of formula (A):

wherein a and a' range from 2 to 150 and b ranges from 1 to 100, and at least one $C_8$-$C_{30}$ fatty alcohol comprising at least one unsaturation;
   wherein the weight ratio of the at least one $C_8$-$C_{30}$ fatty alcohol comprising at least one unsaturation to the at least one polycondensate of ethylene oxide and of propylene oxide ranges from about 0.1 to about 10; and
in a second compartment, a second composition comprising at least one oxidizing agent.

* * * * *